US008784471B2

(12) United States Patent
Rothman (10) Patent No.: US 8,784,471 B2
(45) Date of Patent: Jul. 22, 2014

(54) BLOOD VESSEL PROSTHESIS AND DELIVERY APPARATUS

(71) Applicant: Barts and the London NHS Trust, London (GB)

(72) Inventor: Martin Terry Rothman, London (GB)

(73) Assignee: Barts and the London NHS Trust, London (GB)

( * ) Notice: Subject to any disclaimer, the term of this patent is extended or adjusted under 35 U.S.C. 154(b) by 0 days.

(21) Appl. No.: 13/863,302

(22) Filed: Apr. 15, 2013

(65) Prior Publication Data

US 2013/0231731 A1 Sep. 5, 2013

Related U.S. Application Data

(63) Continuation of application No. 12/439,681, filed on Aug. 3, 2009, now abandoned.

(30) Foreign Application Priority Data

Aug. 31, 2006 (GB) .................................. 06172191.1
Aug. 30, 2007 (WO) ................ PCT/GB2007/003274

(51) Int. Cl.
*A61F 2/06* (2013.01)
*A61F 2/954* (2013.01)
*A61F 2/07* (2013.01)

(52) U.S. Cl.
CPC ........... *A61F 2/954* (2013.01); *A61F 2002/065* (2013.01); *A61F 2/07* (2013.01); *A61F 2002/061* (2013.01)
USPC ......................... 623/1.11; 623/1.13; 623/1.35

(58) Field of Classification Search
USPC ...................................................... 623/1.11
See application file for complete search history.

(56) References Cited

U.S. PATENT DOCUMENTS

| 4,733,665 A | 3/1988 | Palmaz |
|---|---|---|
| 4,739,762 A | 4/1988 | Palmaz |

(Continued)

FOREIGN PATENT DOCUMENTS

| CA | 2580952 A1 | 9/2005 |
|---|---|---|
| EP | 0646365 | 4/1995 |

(Continued)

OTHER PUBLICATIONS (Journal article) K. inoue et al., Aortic Arch Reconstruction by Transluminally Placed Enovascular Branched Stent Graft, Circulation. 1999; 100.

*Primary Examiner* — Thomas J Sweet
*Assistant Examiner* — Brian Dukert
(74) *Attorney, Agent, or Firm* — Steptoe & Johnson LLP (57) ABSTRACT

A method is described for delivering a prosthesis to a branch region of a blood vessel, the branch region having first and second blood vessel branches, the prosthesis comprising a main conduit and first and second branch conduits. The method includes inserting a first guide wire in the blood vessel such that it extends through the blood vessel into the first blood vessel branch; inserting a second guide wire in the blood vessel such that it extends through the blood vessel into the second blood vessel branch; moving the prosthesis to the branch region by moving the first branch conduit along the first guide wire and the second branch conduit along the second guide wire; and moving the first/second branch conduit along the first/second guide wire from a first position in which they project inside the main conduit to a second position in which they project out from the main conduit.

14 Claims, 3 Drawing Sheets

(56) References Cited

U.S. PATENT DOCUMENTS

| | | |
|---|---|---|
| 4,856,516 A | 8/1989 | Hillstead |
| 4,913,141 A | 4/1990 | Hillstead |
| 4,950,227 A | 8/1990 | Savin et al. |
| 5,019,090 A | 5/1991 | Pinchuk |
| 5,037,141 A | 8/1991 | Jardine |
| 5,178,634 A | 1/1993 | Ramos Martinez |
| 5,342,300 A | 8/1994 | Stefanadis et al. |
| 5,360,401 A | 11/1994 | Turnland et al. |
| 5,387,193 A | 2/1995 | Miraki |
| 5,609,627 A | 3/1997 | Goicoechea et al. |
| 5,653,743 A | 8/1997 | Martin |
| 5,709,713 A | 1/1998 | Evans et al. |
| 5,749,825 A | 5/1998 | Fischell et al. |
| 5,755,770 A | 5/1998 | Ravenscroft |
| 5,782,904 A | 7/1998 | White et al. |
| 5,824,040 A | 10/1998 | Cox et al. |
| 5,824,064 A | 10/1998 | Taheri |
| 5,843,158 A | 12/1998 | Lenker et al. |
| 5,904,713 A | 5/1999 | Leschinsky |
| 5,925,061 A | 7/1999 | Ogi et al. |
| 5,984,955 A | 11/1999 | Wisselink |
| 6,099,548 A | 8/2000 | Taheri |
| 6,099,559 A | 8/2000 | Nolting |
| 6,187,033 B1 | 2/2001 | Schmitt et al. |
| 6,334,867 B1 | 1/2002 | Anson |
| 6,344,056 B1 | 2/2002 | Dehdashtian |
| 6,482,228 B1 | 11/2002 | Norred |
| 6,641,606 B2 | 11/2003 | Ouriel et al. |
| 6,730,118 B2 | 5/2004 | Spencer et al. |
| 6,770,090 B2 | 8/2004 | Gantt et al. |
| 6,773,457 B2 | 8/2004 | Ivancev et al. |
| 6,790,230 B2 | 9/2004 | Beyersdorf et al. |
| 6,827,726 B2 | 12/2004 | Parodi |
| 6,860,900 B2 | 3/2005 | Clerc et al. |
| 6,866,650 B2 | 3/2005 | Stevens |
| 6,949,121 B1 | 9/2005 | Laguna |
| 6,989,024 B2 | 1/2006 | Hebert et al. |
| 6,994,700 B2 | 2/2006 | Elkins et al. |
| 7,018,406 B2 | 3/2006 | Seguin et al. |
| 7,037,331 B2 | 5/2006 | Mitelberg et al. |
| 7,041,079 B2 | 5/2006 | Yozu et al. |
| 7,044,966 B2 | 5/2006 | Svanidze et al. |
| 7,201,772 B2 | 4/2007 | Schwammenthal et al. |
| 2002/0082684 A1 | 6/2002 | Mishaly |
| 2003/0004567 A1 | 1/2003 | Boyle et al. |
| 2003/0036791 A1 | 2/2003 | Philipp et al. |
| 2003/0153968 A1 | 8/2003 | Geis et al. |
| 2004/0073288 A1 | 4/2004 | Kerr |
| 2004/0098091 A1 | 5/2004 | Erbel et al. |
| 2004/0116997 A1 | 6/2004 | Taylor et al. |
| 2004/0133266 A1 | 7/2004 | Clerc et al. |
| 2004/0204754 A1 | 10/2004 | Kaplan et al. |
| 2004/0210304 A1 | 10/2004 | Seguin et al. |
| 2005/0131517 A1 | 6/2005 | Hartley et al. |
| 2005/0154444 A1 | 7/2005 | Quadri |
| 2005/0222674 A1 | 10/2005 | Paine |
| 2005/0240257 A1 | 10/2005 | Ishimaru |
| 2006/0004436 A1 | 1/2006 | Amarant et al. |
| 2006/0052865 A1 | 3/2006 | Banas |
| 2006/0069323 A1 | 3/2006 | Elkins et al. |
| 2006/0095118 A1 | 5/2006 | Hartley et al. |
| 2006/0155363 A1 | 7/2006 | Laduca et al. |
| 2006/0155366 A1 | 7/2006 | LaDuca et al. |
| 2006/0224236 A1 | 10/2006 | Thistle |
| 2006/0287717 A1 | 12/2006 | Rowe et al. |
| 2007/0055350 A1 | 3/2007 | Erickson et al. |
| 2007/0083215 A1 | 4/2007 | Hamer et al. |
| 2007/0100440 A1 | 5/2007 | Figulla et al. |
| 2007/0150051 A1 | 6/2007 | Arnault de la Menardiere et al. |
| 2007/0233220 A1 | 10/2007 | Greenan |
| 2011/0288627 A1 | 11/2011 | Hartley et al. |

FOREIGN PATENT DOCUMENTS

| | | |
|---|---|---|
| EP | 0832618 | 4/1998 |
| EP | 1029518 | 8/2000 |
| EP | 1117348 | 7/2001 |
| EP | 1161268 | 12/2001 |
| EP | 1330993 | 7/2003 |
| EP | 1656906 | 5/2006 |
| EP | 1759666 | 3/2007 |
| GB | 2398245 | 8/2004 |
| WO | 91/17720 | 5/1991 |
| WO | 96/24308 | 8/1996 |
| WO | 97/17101 | 5/1997 |
| WO | 98/19629 | 5/1998 |
| WO | 99/36002 | 7/1999 |
| WO | 00/12168 | 3/2000 |
| WO | 00/42948 | 7/2000 |
| WO | 00/44309 | 8/2000 |
| WO | 02/056799 | 7/2002 |
| WO | 02/076346 | 10/2002 |
| WO | 03/065933 | 8/2003 |
| WO | 2003/068302 | 8/2003 |
| WO | 03/082153 | 10/2003 |
| WO | 2005/037141 | 4/2005 |
| WO | 2005/122957 | 12/2005 |
| WO | 2007/026991 | 3/2007 |
| WO | 2007/028112 | 3/2007 |
| WO | 2007/051179 | 5/2007 |
| WO | 2007/058857 | 5/2007 |
| WO | 2007/071436 | 6/2007 |
| WO | 2007/079081 | 7/2007 |
| WO | 2007/081820 | 7/2007 |
| WO | 2007/146021 | 12/2007 |

BLOOD VESSEL PROSTHESIS AND DELIVERY APPARATUS

CROSS-REFERENCE TO RELATED APPLICATIONS

This application is a continuation of U.S. patent application Ser. No. 12/439,681, filed Aug. 3, 2009, which claims priority to International Application No. PCT/GB2007/003274, filed on Aug. 30, 2007, which claims priority to Great Britain Patent Application No. 06172191.1, filed Aug. 31, 2006, each of which is incorporated by reference in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE DISCLOSURE

The disclosure relates generally to a prosthesis for a blood vessel, a delivery apparatus for delivering the prosthesis to the blood vessel, and related methods thereof.

BACKGROUND

Aneurysms are permanent distensions of the wall of a blood vessel, e.g., an artery, which disrupt the haemodynamics of the blood vessel. The aneurysm may halt the flow of blood at certain regions of the blood vessel, increasing the risk of clot formation, which may in turn cause a cerebral embolism. Furthermore, a reduction in the structural wall integrity of the blood vessel may occur, which can cause a reduction in the effectiveness of the blood vessel and put a higher strain on the heart muscle, increasing the risk of heart failure or vessel rupture.

Dissections are tears in the blood vessel's intima or delaminations of the collagen/elastin wall architecture of the blood vessel. Dissections can result in a false lumen, i.e., inner cavity, within the blood vessel. The false lumen may provide areas in which blood can pool, increasing the risk of clot formation and subsequent cerebral embolism. Severe dissection may even result in a breach of the blood vessel integrity and possible bleeding from the blood vessel e.g., into the thoracic cavity, which may cause death in a short period of time.

Traditional treatment for dissections and aneurysms include surgical resection, removing the offending tissue (depending on the extent of the damage to the blood vessel), or the insertion of a tubular prosthesis or stent grant within the lumen of the blood vessel to remove the mechanical loading on the damaged blood vessel wall and to provide a haemodynamically-compatible conduit for the transport of blood. Prostheses are traditionally made from Dacron® or high density Polytetrafluoroethylene (PTFE).

More recently, endovascular methods of prosthesis introduction have reduced health risks to the patient by allowing percutaneous introduction of the prosthesis via the femoral artery. Operations can therefore be conducted under local anaesthetic, and cardiac arrest and/or cardiac bypass procedures may be eliminated, reducing the overall cost of the treatment.

Prostheses and stent grafts have been designed for positioning at bifurcation regions of blood vessels, i.e., regions in which the blood vessel branches. For example, PCT Application nos. W000042948, W003082153 and W005122957 and U.S. Pat. No. 5,984,955 disclose bifurcated prostheses/stent grafts for positioning primarily at the iliac bifurcation of the aorta. The prostheses comprise a main conduit, a first branch conduit extending therefrom, and a removable or retractable second branch conduit. The main conduit is designed to locate within the aorta and the first and second branch conduits are designed to locate within respective iliac arteries.

Journal article: K. Inoue et al, Aortic Arch Reconstruction by Transluminally Placed Endovascular Branched Stent Graft," Circulation, 1999; 100 describes a stent graft which includes conduits for aortic branches and a method of introduction.

The prostheses/stent grafts described above are generally sited percutaneously using a catheter delivery system which allows introduction to and guidance through the vasculature. Control of the device is made through pushrods or hypotubes which can extract the device from a casing and locate it in position.

Notably, none of these prostheses and stent grafts, or the delivery systems thereof, are intended for, or are indeed appropriate for, positioning at the branch region of the ascending aorta where the aortic root meets the right and left coronary arteries, which feed the heart muscle with oxygenated blood. The anatomy of the aortic root and the coronary arteries is complex. This location is particularly prone to aneurysms and dissections.

SUMMARY

According to a first aspect of some disclosed embodiments, there is provided a prosthesis delivery apparatus for delivering a prosthesis to the branch region of the ascending aorta and the right and left coronary arteries, the apparatus comprising: a prosthesis comprising a main conduit and first and second branch conduits, a first guide wire for inserting in the ascending aorta such that it extends through the ascending aorta into the right coronary artery; and a second guide wire for inserting in the ascending aorta such that it extends through the ascending aorta into the left coronary artery; wherein the prosthesis is arranged such that: the first and second branch conduits are movable along the first and second guide wires to the branch region, and the first branch conduit is moveable from a first position in which it projects inside the main conduit, to a second position in which it projects out from the main conduit for location in the right coronary artery, the first branch conduit being arranged to turn inside out as it moves from the first position to the second position, and the second branch conduit is movable from a first position in which it projects inside the main conduit to a second position in which it projects out from the main conduit for location in the left coronary artery, the second branch conduit being arranged to turn inside out as it moves from the first position to the second position.

According to a second aspect of some disclosed embodiments, there is provided a method for delivering a prosthesis to the branch region of the ascending aorta and the right and left coronary arteries, the prosthesis comprising a main conduit and first and second branch conduits, the method comprising: inserting a first guide wire in the ascending aorta such that it extends through the ascending aorta into the right coronary artery; inserting a second guide wire in the ascending aorta such that it extends through the ascending aorta into the left coronary artery; moving the prosthesis to the branch region by moving the first branch conduit along the first guide wire and the second branch conduit along the second guide wire; and moving the first branch conduit along the first guide wire from a first position in which it projects inside the main conduit to a second position in which it projects out from the main conduit, to locate the first branch conduit in the right coronary artery, the first branch conduit turning inside out as it moves from the first position to the second position; moving the second branch conduit along the second guide wire from a first position in which it projects inside the main conduit to a second position in which it projects out from the main conduit, to locate the second branch conduit in the left coronary artery, the second branch conduit turning inside out as it moves from the first position to the second position.

Preferably, the prosthesis is mounted on the first and second guide wires, by inserting the first and second guide wires through the first and second branch conduits respectively, prior to moving the branch conduits toward the branch region.

According to a third aspect of some disclosed embodiments, there is provided a prosthesis for locating at the branch region of the ascending aorta and the right and left coronary arteries, the prosthesis comprising a main conduit and first and second branch conduits, the first branch conduit being for locating in the right coronary artery and the second branch conduit being for locating in the left coronary artery, wherein the first branch conduit is movable from a first position in which it projects inside the main conduit to a second position in which projects out from the main conduit in order for it to locate in the right coronary artery, the first branch conduit being arranged to turn inside out as it moves from the first position to the second position, and the second branch conduit is movable from a first position in which it projects inside the main conduit to a second position in which it projects out from the main conduit in order for it to locate in the left coronary artery, the second branch conduit being arranged to turn inside out as it moves from the first position to the second position.

This arrangement of the branch conduits described above permits the prosthesis to take a compact shape during delivery to the branch region of the blood vessel. Thus, the possibility of obstruction of the prosthesis during delivery is reduced. Furthermore, by arranging the branch conduits to turn inside out, moving the branch conduit from the first to the second position may be straightforward, and construction of the branch conduits may be uncomplicated. The prosthesis may be manufactured in one piece.

Preferably, the prosthesis used in the delivery apparatus according to the first aspect of some disclosed embodiments and/or of the prosthesis used in the method according to the second aspect of some disclosed embodiments is a prosthesis according to the third aspect of some disclosed embodiments. The prosthesis may be used to treat aneurysms or dissections of the ascending aorta proximal to the aortic valve and the left ventricle of the heart.

According to a fourth aspect of some disclosed embodiments, there is provided a prosthesis delivery apparatus for delivering a prosthesis to a branch region of a blood vessel, the branch region having first and second blood vessel branches, the apparatus comprising: a prosthesis comprising a main conduit and first and second branch conduits, a first guide wire for inserting in the blood vessel such that it extends through the blood vessel into the first blood vessel branch; and a second guide wire for inserting in the blood vessel such that it extends through the blood vessel into the second blood vessel branch; wherein the prosthesis is arranged such that the first branch conduit is movable along the first guide wire toward the first blood vessel branch for location in the first blood vessel branch, and the second branch conduit is movable along the second guide wire toward the second blood vessel branch for location in the second blood vessel branch.

According to a fifth aspect of some disclosed embodiments, there is provided a method for delivering a prosthesis to a branch region of a blood vessel, the branch region having first and second blood vessel branches, the prosthesis comprising a main conduit and first and second branch conduits, the method comprising: inserting a first guide wire in the blood vessel such that it extends through the blood vessel into the first blood vessel branch; inserting a second guide wire in the blood vessel such that it extends through the blood vessel into the second blood vessel branch; moving the first branch conduit along the first guide wire toward the first blood vessel branch for location in the first blood vessel branch and moving the second branch conduit along the second guide wire toward the second blood vessel branch for location in the second blood vessel branch.

Preferably, in the fourth and fifth aspects of some disclosed embodiments, the prosthesis is mounted on the first and second guide wires by inserting the first and second guide wires through the first and second branch conduits respectively, prior to moving the branch conduits toward the first and second blood vessel branches.

According to a sixth aspect of some disclosed embodiments, there is provided a prosthesis for locating at a branch region of a blood vessel, the branch region having a first blood vessel branch, the prosthesis comprising a main conduit and a first branch conduit, the first branch conduit being for locating in the first blood vessel branch, wherein the first branch conduit is movable from a first position in which it projects inside the main conduit to a second position in which projects out from the main conduit in order for it to locate in the first blood vessel branch, the first branch conduit being arranged to turn inside out as it moves from the first position to the second position.

Preferably, in the sixth aspect of some disclosed embodiments, the prosthesis comprises a second branch conduit, the second branch conduit being for locating in a second blood vessel branch of the branch region. Preferably, the second branch conduit is movable from a first position in which it projects inside the main conduit to a second position in which it projects out from the main conduit in order for it to locate in the second blood vessel branch, the second branch conduit being arranged to turn inside out as it moves from the first position to the second position.

This arrangement of the branch conduit(s) permits the prosthesis to take a compact shape during delivery to the branch region of the blood vessel. Thus, the possibility of obstruction of the prosthesis during delivery is reduced. Furthermore, by arranging the branch conduit(s) to turn inside out, moving the branch conduit(s) from the first to the second position may be straightforward, and construction of the branch conduit(s) may be uncomplicated. The prosthesis may be manufactured in one piece.

In various aspects of some disclosed embodiments, preferably, the main conduit comprises a first end which defines an opening, a second end which defines an opening, and a sidewall extending between the first and second ends. Preferably, the first and second branch conduits are mounted to opposing flanks of the sidewall of the main conduit. Preferably, the first and second branch conduits and the main conduit are in one piece.

The main conduit may be substantially cylindrical. The cross-section of the main conduit, in a plane substantially perpendicular to the longitudinal axis of the main conduit, may therefore be substantially circular. In this description, the term, "mounted to opposing flanks" is intended to mean that the first and second branch conduits are mounted to the sidewall at positions which are more than 90 degrees apart, preferably more than 150 degrees apart, about the circumference of the circle or other cross-sectional shape. The first and second branch conduits may be mounted at positions of the sidewall that are offset in a direction parallel to the longitudinal axis of the main conduit.

According to a seventh aspect of some disclosed embodiments, there is provided a prosthesis for locating at a branch region of a blood vessel, the branch region having first and second blood vessel branches, the prosthesis comprising: a main conduit and first branch and second branch conduits, the main conduit having a first end which defines an opening, a second end which defines an opening, and a side wall extending between the first and second ends, the first and second branch conduits being for locating in the first and second blood vessel branches respectively, wherein the first and second branch conduits are mounted to opposing flanks of the sidewall of the main conduit, and the main conduit and first and second branch conduits are one piece.

Preferably, the prosthesis used in the delivery apparatus according to the fourth aspect of some disclosed embodiments, and/or the prosthesis used in the method according to the fifth aspect of some disclosed embodiments, is a prosthesis according to the sixth or seventh aspect of some disclosed embodiments.

In the fourth, fifth, sixth and seventh aspects of some disclosed embodiments, preferably, the blood vessel is an artery, preferably the aorta, most preferably the ascending aorta. Preferably, the first and second blood vessel branches are the left and right coronary arteries. Thus, the prosthesis may be used to treat aneurysms or dissections of the ascending aorta proximal to the aortic valve and the left ventricle of the heart.

In the various aspects of some disclosed embodiments, preferably, one or more first actuators are provided to move the first and second branch conduits from the first to the second position. Preferably, the first actuators are push rods. The push rods may be slidably mounted on the guide wires. Thus, since the guide wires are located in the blood vessel branches, the push rods may push the branch conduits in the appropriate directions for location in the blood vessel branches (e.g., the left and right coronary arteries), simply by sliding along the guide wires.

Preferably, first and second push rods are provided as first actuators, the first push rod being arranged to push the first branch conduit and the second push rod being arranged to push the second branch conduit. Preferably, the first and second push rods are slidably mounted on the first and second guide wires respectively. The first and second guide wires may extend through a portion of, or all of, the first and second push rods respectively. For example, the guide wires may extend through the first and second push rods at positions within the prosthesis, but be separated from the push rods at positions outside the prosthesis. The guide wires may extend out of the push rods via one or more side holes.

Preferably, one or more second actuators are provided to push the prosthesis, e.g., the main conduit of the prosthesis, toward the branch region of the blood vessel, which in turn causes the first and second branch conduits to move along the first and second guide wires respectively. Preferably, the second actuator can also move the prosthesis in the opposite direction, i.e., in a direction away from the branch region.

Thus, the first and second actuators may work against each other, e.g., so that the main conduit of the prosthesis can be held stationary whilst the branch conduits are moved from the first position to the second position. The second actuators may be one or more push rods. The first actuator push rods may be arranged to extend through one or more conduits provided by the second actuator push rods.

Preferably, the first and/or second guide wire comprises an identifying mark or shape. Thus, the appropriate guide wire can be chosen for each blood vessel branch.

Preferably, the prosthesis is expandable from a contracted state to an expanded state. Accordingly, the prosthesis may be placed in a contracted position during delivery to the branch region, so that it is less likely to be obstructed during delivery. Then, once positioned at the branch region, it may be expanded to a desired size for use.

Preferably, a delivery casing is provided for holding the prosthesis in a contracted state during delivery of the prosthesis to the branch region. Preferably, the prosthesis is arranged to expand automatically upon removal of the delivery casing. The delivery casing may be a sleeve that surrounds the prosthesis to maintain it in a contracted state. The delivery casing may be elongated and may act as the second actuator for pushing the prosthesis to the branch region of the blood vessel.

The prosthesis may be resiliently biased when positioned in the contracted state such that, upon removal of the delivery casing, the prosthesis expands automatically. The prosthesis may be formed of PTFE, Nylon, and the like. The prosthesis may be resiliently biased by shape-memory alloy elements, e.g., formed of Nitinol, embedded therein.

By locating in the blood vessel branches (e.g., the right and left coronary arteries), the first and second branch conduits may be used to anchor the prosthesis in position; prevent occlusion of the opening between the blood vessel branches, into which they locate, and the blood vessel (e.g., the ascending aorta); and/or help maintain the main conduit in the expanded state.

A fixing means may be provided for fixing the first and second branch conduits in position in the respective first and second blood vessel branches. The fixing means may be integral with the branch conduits. For example, the fixing means may be one or more stents attached to, e.g., an end of the branch conduits. Balloons may be provided on the first actuators, e.g., push rods, to expand the stents in order to fix the branch conduits in position. The first actuators, e.g., push rods, may be used to hold the branch conduits in position prior to fixing, to prevent e.g., retraction of the branch conduits from the blood vessel branches. Alternatively, separate fixing means may be provided to fix the branch conduits in position, e.g., after the push rods have been retracted. For example, independent stents or endovascular staples may be used.

A fixing means may be provided at one or both ends of the main conduit. The fixing means may be used to anchor the respective ends of the main conduit against the blood vessel wall in order to prevent blood ingress between the main conduit and the blood vessel wall. The fixing means may be integral with the respective ends of the main conduit. For example, the fixing means may be one or more stents attached to the ends, the stents being expandable, e.g., by balloons. Alternatively, separate fixing means may be provided to fix the main conduit in position, e.g., after the first actuator push rods have been retracted. For example, independent stents, or endovascular staples may be used.

Preferably, the prosthesis and/or the guide wires are configured for insertion into the blood vessel percutaneously. Thus, an endovascular method of prosthesis delivery may be provided.

By having open first and second ends of the main conduit, blood may flow between the blood vessel and the main conduit. The guide wires and/or actuators (e.g., push rods) may extend through the main conduit via the opening of the first end. Preferably, the second end of the main conduit is for locating adjacent the aortic valve. The second end of the main conduit may comprise an artificial aortic valve.

Preferably, the first and second branch conduits are connected to the side wall of the main conduit such that blood may flow between the first and second branch conduits and the main conduit. By connecting the branch conduits to the side wall, rather than the second end for example, an appropriate configuration may be achieved for positioning the prosthesis e.g. at the branching of the aortic root and the right and left coronary arteries. In particular, this arrangement may permit the branch conduits to project in directions substantially opposite from each other, and substantially perpendicular to the longitudinal axis of the main conduit. Thus, the prosthesis may conform to the complex anatomy of the bifurcation of the aortic root and the right and left coronary arteries.

BRIEF DESCRIPTION OF THE DRAWING

An example embodying some disclosed embodiments is now described with reference to the accompanying drawings, in which.

DETAILED DESCRIPTION

Some embodiments of a delivery apparatus and/or methods are disclosed herein for delivering a prosthesis to a branch region of a blood vessel, as shown in FIGS. 1a-1c and FIGS. 2a-2d. In this embodiment, the blood vessel is the ascending aorta 1 of a human, and the branch region is the region at the aortic root 11, where the right and left coronary arteries 12, 13 connect to the aorta 1, adjacent to the aortic valve 15.

Figure 1A:
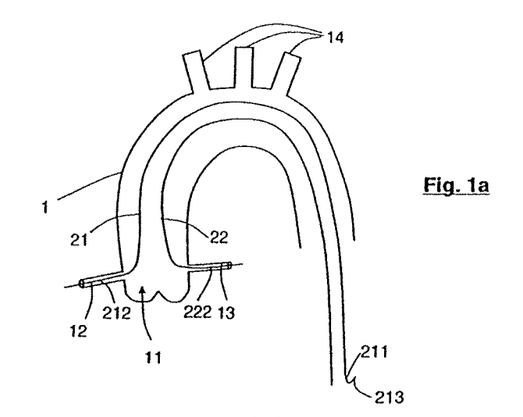
FIG. 1a shows guide wires of a delivery apparatus extending through a blood vessel to a branch region of the blood vessel.
Figure 1B:
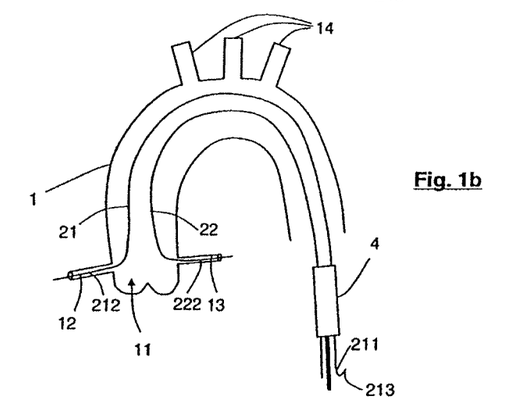
FIGS. 1b and 1c show a prosthesis mounted on the guide wires of FIG. 1a and moved towards the branch region of the blood vessel.
Figure 1C:
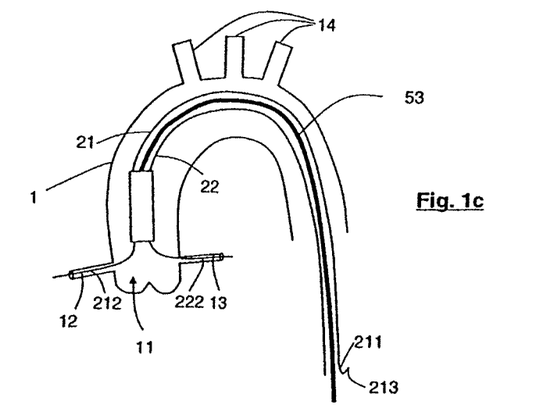

The delivery apparatus comprises first and second guide wires 21, 22, a prosthesis 3, a prosthesis delivery casing 4, and first and second push rods 51, 52. The prosthesis 3 is formed from haemodynamically-compatible material and comprises a main conduit 33 having a first end 331, a second end 332 and side wall 34 extending between the first and second ends 331, 332. The first and second ends 331, 332 are open. The prosthesis 3 comprises first and second branch conduits 31, 32, which are connected at respective first ends 311, 321 to opposite flanks of the side wall 34. The first ends 311, 321 of the branch conduits 31, 32 are open to permit blood flow between the branch conduits 31, 32 and the main conduit 33. The second ends 312, 322 of the branch conduits 31, 32 are also open, to permit blood flow between the branch conduits 31, 32 and the coronary arteries 12, 13.

The steps undertaken to deploy the prosthesis 3, using the delivery apparatus, are described below.

Firstly, with reference to FIGS. 1a to 1c, the first guide wire 21 is percutaneously inserted into the aorta 1 such that it extends through the aorta 1, and a first end 212 of the first guide wire 21 is positioned in the right coronary artery 12. The first guide wire 21 may be placed in this position using a catheter (not shown), which is subsequently removed.

Next, the second guide wire 22 is percutaneously inserted into the aorta 1 such that it extends through the aorta 1, and a first end 222 of the second guide wire 22 is positioned in the left coronary artery 13. The second guide wire 22 may also be placed in this position using a catheter (not shown), which is subsequently removed.

Next, the prosthesis 3, surrounded by the delivery casing 4, is mounted on the first and second guide wires 21, 22 and pushed by a push rod 53 along the guide wires 21, 22, past the aortic branch arteries 14, toward the aortic root 11, as shown in FIGS. 1b and 1c.

Figure 2A:
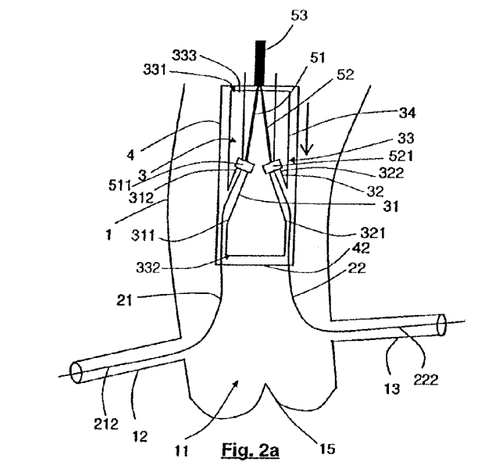
FIGS. 2a to 2d show successive steps performed during the location of branch conduits of the prosthesis of FIGS. 1b and 1c into blood vessel branches of the branch region of the blood vessel.

As can be seen in FIG. 2a, which shows a cross-section of the prosthesis 3 mounted on the first and second guide wires 21, 22, during delivery to the aortic root region 11, the first and second branch conduits 31, 32 are in a first position in which they project into the interior of the main conduit 33. Furthermore, the main conduit 33 is held in a contracted state by the delivery casing 4. The delivery casing 4 is a removable sleeve that surrounds and compresses the main conduit 33. Accordingly, the prosthesis 3 may take a compact shape during delivery to the aortic root region 11, reducing the chance of the prosthesis 3 being obstructed on the way.

In the first position, the first and second branch conduits 31, 32 are inclined from the sidewall 34. The first and second branch conduits 31, 32 project toward the first end opening 333 of the main conduit 3. As shown in FIG. 2a, the first and second guide wires 21, 22 extend into the main conduit 33 via the first end opening 333 of the main conduit 33, and through the first and second branch conduits 31, 32 via the open second ends 312, 322 of the first and second branch conduits 31, 32. The first and second guide wires 21, 22 then project from the prosthesis 3 via the first ends 311, 321 of the first and second branch conduits 31, 32, whereupon they extend between the sidewall 34 and the delivery casing 4, and then through an opening 42 of the delivery casing 4.

Once the prosthesis 3 has reached the aortic root region 11, deployment of the prosthesis 3 takes place as described below with respect to FIGS. 2b to 2d.

Figure 2B:
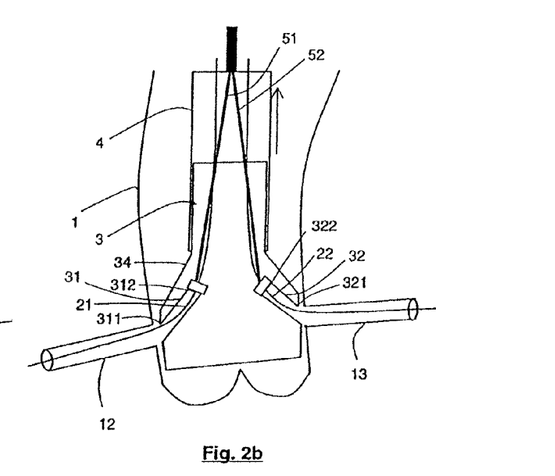
Figure 2C:
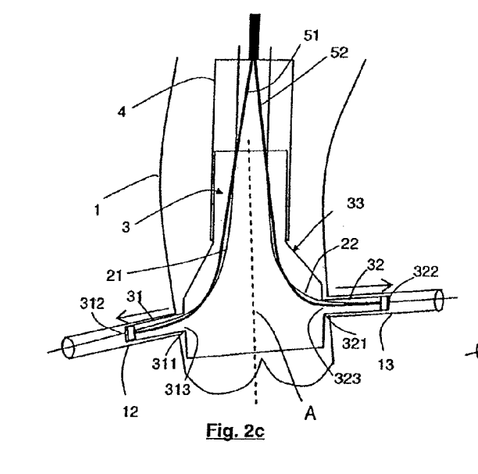
Figure 2D:
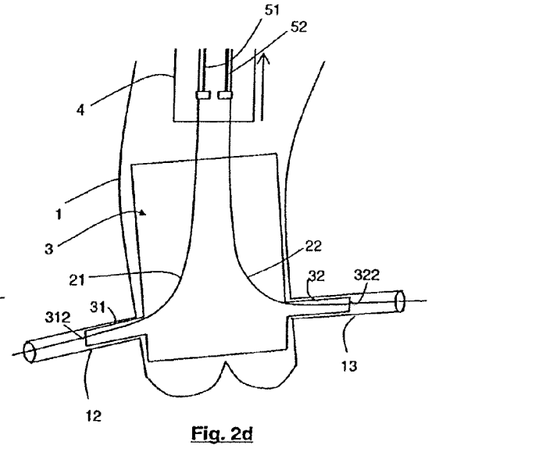

Firstly, the delivery casing 4 is partially removed from the prosthesis 3, so that the first ends 311, 321 of the first and second branch conduits 31, 32 are exposed, as shown in FIG. 2b. The main conduit 33 of the prosthesis 3 comprises shape memory alloy elements, such that, upon removal of the delivery casing 4, the main conduit 33 expands automatically. Once the first ends 311, 321 of the first and second branch conduits 31, 32 are exposed, first and second push rods 51, 52, which have engagement surfaces 511, 521, that abut the second ends 312, 322 of the first and second branch conduits 31, 32, are manually controlled to push the second ends 312, 322 of the branch conduits through the open first ends 311, 321 of the first and second branch conduits 31, 32. This causes the branch conduits 31, 32 to avert, i.e., turn inside out, whereupon they are placed in a second position, as shown in FIG. 2c, in which they project outward from the main conduit 33 of the prosthesis 3. In the second position, the branch conduits 31, 32 project in a direction substantially perpendicular to the longitudinal axis of the main conduit 33, indicated generally by line A.

As the first and second branch conduits 31, 32 are moved from the first position to the second position, by the push rods 51, 52, they are forced into the right and left coronary arteries respectively. This helps anchor the prosthesis 3 in position, ensures that the fluid path between the aorta 1 and the coronary arteries 12, 13 is kept open, and helps maintain the main conduit 33 in the expanded state.

Next, the delivery casing is removed fully from the prosthesis, such that the entire main conduit 33 can expand to substantially the size of the inner wall diameter of the aorta 1. The push rods 51, 52 are also retracted. To secure the prosthesis 3 in position, stents (not shown) can be used.

Thus, the prosthesis 3 may reduce mechanical loading on the aorta 1 at the aortic root region 11, and may provide a haemodynamically compatible conduit for the transport of blood between the aorta and the right and left coronary arteries.

Subsequently, the first and second guide wires 21, 22 can be removed.

In FIG. 2a, it can be seen that the first and second branch conduits 31, 32 are mounted to opposite flanks of the sidewall 34 at points level with one another, i.e., the mounting points are generally aligned in a direction parallel to the longitudinal axis A of the main conduit 33. However, the mounting points may be offset in a direction parallel to the longitudinal axis A of the main conduit 33. This may be particularly useful to enable compact packing of the prosthesis 4; it may mean that the branch conduits 31, 32 do not obstruct each other if the prosthesis 4 is compressed.

Figure 3:
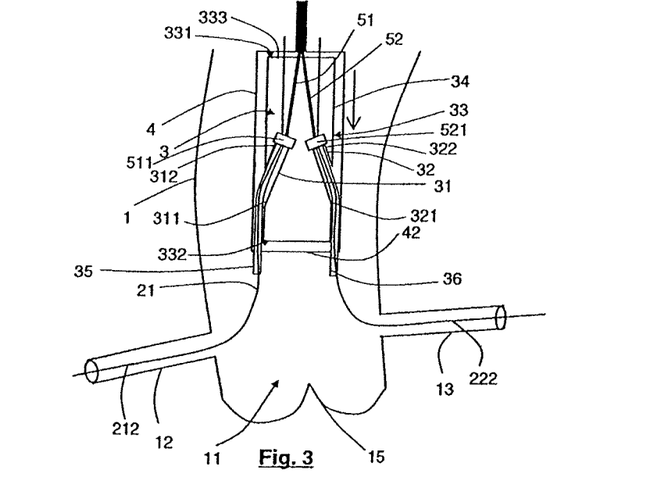
FIG. 3 shows a delivery apparatus according to a second embodiment.

FIG. 3 shows a delivery apparatus according to a second embodiment of the delivery apparatus and method. The delivery apparatus is similar to and functions in generally the same way as the apparatus of the first embodiment, except that the prosthesis in this second embodiment comprises two guide tubes 35, 36. The guide tubes 35, 36 are provided to make mounting of the prosthesis, on the guide wires 21, 22, simpler. The same numbering is used to indicate features common to FIG. 3 and FIGS. 1a to 2d.

As shown in FIG. 3, the guide tubes 35, 36 each fit into the first and second branch conduits 31, 32 respectively, when the branch conduits 31, 32 are in their first positions.

The guide tubes 35, 36 extend through the branch conduits 31, 32 and through the first ends 311, 321 of each branch conduit 31, 32, whereupon they extend between the sidewall 34 and the delivery casing 4 and through the opening 42 of the delivery casing 4, and then project from the prosthesis 4.

Since the guide tubes 35, 36 project from the prosthesis 4, the guide wires 21, 22 can easily be inserted into the guide tubes 35, 36, whereupon the guide tubes 35, 36 serve to channel the guide wires 21, 22 between the delivery casing 4 and the sidewall 34, through the branch conduits 31, 32 and through the main conduit 33 of the prosthesis. Thus, mounting of the prosthesis on the guide wires is made easier.

The guide tubes 35, 36 are connected to the prosthesis 4; however, alternatively, the guide tubes 35, 36 can be connected to the push rods 51, 52.

FIGS. 4a to 4e show a branch conduit 32' a push rod 52' of a delivery apparatus according to a third embodiment of some disclosed embodiments. The branch conduit 32' is similar to the branch conduits 31, 32 of the previous embodiments of the invention, and it functions in generally the same way, except that it comprises an integral stent 61, located at its second end 322'. The branch conduit 32' can be used as an alternative to the branch conduits 31, 32 of the previous embodiments. The stent 61 is provided as a fixing means, to fix the branch conduit 32' in position once it is located in the appropriate blood vessel branch. The push rod 52' is similar to the push rods 51, 52 of the previous embodiments of the delivery apparatus and method, and functions in generally the same way as in these previous embodiments, except that it comprises an inflatable balloon 62. The balloon 62 is provided to expand the stent 61.

Figure 4A:
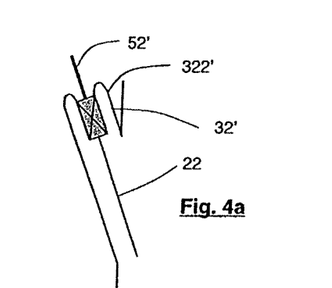
FIGS. 4a to 4e show a branch conduit of a prosthesis according to a third embodiment.
Figure 4B:
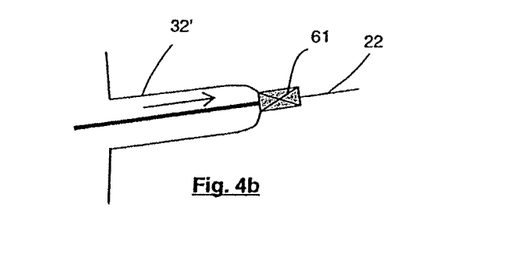
Figure 4C:
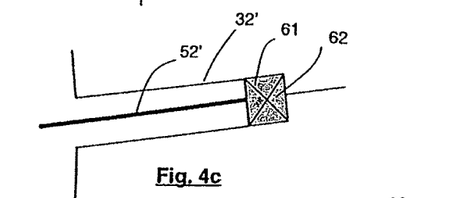
Figure 4D:
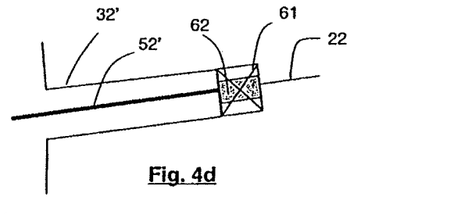
Figure 4E:
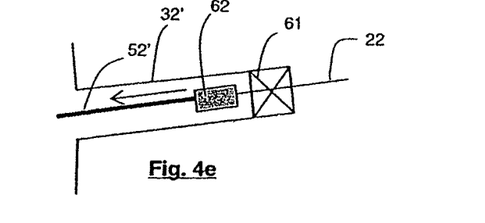

The steps taken to deploy the branch conduit 32' can be seen in FIGS. 4a to 4e. In FIG. 4a, the branch conduit 32' is located in its first position, i.e., in a position in which it is located inside the main conduit of the prosthesis. From the position shown in FIG. 4a, the branch conduit 32' is forced along the guide wire 22 to its second position, as shown in FIG. 4b, by the push rod 52'. The branch conduit 32' averts as it moves from the first to the second position, but the stent 61 does not avert. Once the branch conduit 32' is in the second position, the balloon 62 is inflated, which forces the stent 61 to expand, as shown in FIG. 4c. This causes the stent 61 to press the branch conduit 32 against the side walls of the blood vessel, fixing the branch conduit 32' in position. Once the branch conduit 32' is fixed in position, the balloon 62 is deflated as shown in FIG. 4d. Then, the push rod 52', including the balloon 62, is retracted, as shown in FIG. 4e.

Furthermore, the various embodiments described above are provided by way of illustration only and should not be construed to limit the invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A method for delivering a prosthesis to a branch region of a blood vessel, the branch region having first and second blood vessel branches, the prosthesis comprising a main conduit and first and second branch conduits, the method comprising:
    inserting a first guide wire in the blood vessel such that it extends through the blood vessel into the first blood vessel branch;
    inserting a second guide wire in the blood vessel such that it extends through the blood vessel into the second blood vessel branch;
    moving the prosthesis to the branch region by moving the first branch conduit along the first guide wire and the second branch conduit along the second guide wire; and
    moving the first branch conduit along the first guide wire from a first position in which it projects inside the main conduit to a second position in which it projects out from the main conduit, to locate the first branch conduit in the first blood vessel branch, the first branch conduit turning inside out as it moves from the first position to the second position;
    moving the second branch conduit along the second guide wire from a first position in which it projects inside the main conduit to a second position in which it projects out from the main conduit, to locate the second branch conduit in the second blood vessel branch, the second branch conduit turning inside out as it moves from the first position to the second position.

2. The method of claim 1, wherein one or more actuators are used for moving the first branch and second branch conduits along the first and second guide wires to the branch region.

3. The method of claim 1, wherein one or more actuators are used for moving the first and second branch conduits from the first to the second position.

4. The method of claim 2, wherein the same actuators are used to move the first branch and second branch conduits along the first and second guide wires toward the branch region and to move the first and second branch conduits from the first to the second position.

5. The method of claim 2, wherein the actuators are push rods.

6. The method of claim 5, wherein the push rods are slidably mounted on the guide wires.

7. The method of any one of claim 1, wherein the first and/or second guide wire comprises an identifying mark or shape.

8. The method of any one of claim 1, wherein the first and/or second guide wire is inserted into the blood vessel percutaneously.

9. The method of any one of claim 1, wherein the prosthesis is inserted into the blood vessel percutaneously.

10. The method of any one of claim 1, wherein the prosthesis is expanded from a collapsed state to an expanded state at the branch region.

11. The method of claim 10, wherein a delivery casing is provided for holding the prosthesis in a collapsed state during delivery of the prosthesis to the branch region.

12. The method of claim 11, wherein the prosthesis expands automatically upon removal of the delivery casing.

13. The method of any one of claim 1, wherein one or more stents are used to secure the prosthesis at the branch region.

14. The method of claim 1, wherein the blood vessel is an ascending aorta and the first and second blood vessel branches are left and right coronary arteries.

* * * * *